United States Patent [19]

DiMenna et al.

[11] Patent Number: 4,539,328
[45] Date of Patent: Sep. 3, 1985

[54] NEMATICIDAL ISOTHIAZOLE DERIVATIVES

[75] Inventors: William S. DiMenna, East Amherst, N.Y.; David M. Floyd, Pennington, N.J.

[73] Assignee: FMC Corporation, Philadelphia, Pa.

[21] Appl. No.: 478,959

[22] Filed: Mar. 25, 1983

[51] Int. Cl.³ .................... C07D 275/02; A01N 43/80
[52] U.S. Cl. ..................................... 514/372; 548/214
[58] Field of Search ........................ 548/214; 424/270

[56] References Cited

U.S. PATENT DOCUMENTS 4,053,479 10/1977 Miller et al. ................. 260/302 A
4,346,094 8/1982 Beck et al. .......................... 424/270

OTHER PUBLICATIONS

Burger, Alfred, *Medicinal Chemistry*, Wiley-Interscience, New York (1971), pp. 50, 51, 55.
Imahori, et al., "Isothiazole Azo Dyes," *Chem. Abst.* 88: 75295(a).
K. Gewald and P. Bellmann, *Liebigs Ann. Chem.* 1979, 1534–1546.

*Proceedings of the Helminthological Society of Washington*, 22, pp. 87–89 (1955).

*Primary Examiner*—Donald G. Daus
*Assistant Examiner*—G. Hendricks
*Attorney, Agent, or Firm*—R. L. Hansen; H. R. Ertelt

[57] ABSTRACT

Nematicidal 3-aryl-4-amino-5-isothiazole acids, esters and amides of the formula

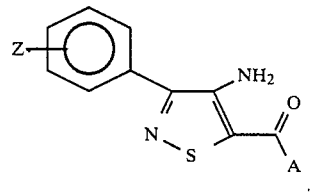

wherein
A is selected from hydroxy, alkoxy, phenylmethoxy, and —NHR, where R is hydrogen, alkyl, 2-hydroxyethyl or 2-acetyloxyethyl; and
Z is selected from hydrogen, halogen, alkyl, alkoxy, difluoromethoxy, thiomethyl, nitro, amino, and phenyl.

1 Claim, No Drawings

NEMATICIDAL ISOTHIAZOLE DERIVATIVES

This invention relates to chemical compositions as well as a method of using the compositions to control nematodes, especially on agricultural crops. More specifically, the nematicidal compositions contain a 3-aryl-4-amino-5-isothiazolecarboxylic acid, ester or amide as the nematicidal agent.

U.S. Pat. No. 4,346,094 discloses a series of 3-aryl-4-amino-5-isothiazolecarboxylic acids, esters and amides useful for the treatment of gout in mammals. U.S. Pat. No. 4,053,479 discloses certain 3-alkoxyisothiazoles and their nematicidal activity. It has now been found that certain 3-aryl-4-amino-5-isothiazole derivatives, some of which are disclosed in U.S. Pat. No. 4,346,094, are effective nematicidal agents. These agents are characterized by nematicidal activity at lower application rates than reported for the 3-alkoxyisothiazoles.

According to the present invention, 3-aryl-4-amino-5-isothiazole derivatives of the following structural formula control nematodes when applied to soil or other locus per se or as suitably formulated nematicidal compositions

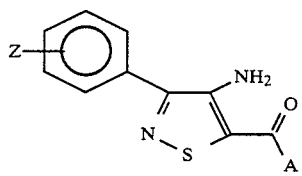

wherein
- A is selected from hydroxy, lower alkoxy, phenylmethoxy, and —NHR, where R is hydrogen, straight chain alkyl of 1–4 carbon atoms, 2-hydroxyethyl or 2-acetyloxyethyl; and
- Z is selected from hydrogen, halogen, lower alkyl, straight or branched chain alkoxy of 1–4 carbon atoms, difluoromethoxy, thiomethyl, nitro, amino, and phenyl; with the proviso that Z is not 2-bromo or 4-nitro when A is ethoxy.

For purposes herein, "lower" as used in "lower alkyl" and "lower alkoxy" means a straight or branched chain of 1–4 and 1–7 (preferably 1–4) carbon atoms, respectively; "halo" or "halogen" means fluorine, chlorine, and bromine.

Certain of the aforesaid nematicidal 3-aryl-4-amino-5-isothiazole derivatives are novel compounds, and these compounds are also within the scope of this invention. In these novel compounds either A is phenylmethoxy and Z is as defined above, or A is selected from hydroxy, lower alkoxy, and —NHR, where R is as defined above, and Z is selected from difluoromethoxy, thiomethyl, nitro, amino, and phenyl.

Among the nematicidal 3-aryl-4-amino-5-isothiazole derivatives, it is preferred that lower alkyl and lower alkoxy be methyl and methoxy, respectively. Preferred compounds include those wherein the substituent Z is in the 4-position, e.g., 4-fluoro. An especially active compound is ethyl 3-(4-fluorophenyl)-4-amino-5-isothiazolecarboxylate.

The nematicidal 3-aryl-4-amino-5-isothiazole derivatives of this invention are generally prepared from appropriately substituted phenylacetonitriles, many of which are commercially available, by the method described as "Procedure A" in U.S. Pat. No. 4,346,094. These syntheses are illustrated below.

EXAMPLE 17

Ethyl 3-(4-Fluorophenyl)-4-amino-5-isothiazolecarboxylate

4-Fluorophenylacetonitrile (50.0 g, 0.37 mole) in 100 ml of methanol was cooled to 0° C., and sodium hydroxide (14.8 g, 0.37 mole) was added portionwise, followed by tert-butyl nitrite (45.6 g, 0.44 mole). Upon complete addition, the reaction mixture was stirred for 16 hours and allowed to warm to room temperature. The reaction mixture was concentrated under reduced pressure to a solid yellow residue. The solid was slurried with a mixture of 300 ml toluene and 500 ml water and the layers separated. The toluene layer was washed with 100 ml of water. The aqueous layers were combined and acidified with concentrated hydrochloric acid to pH 3. 2-(4-Fluorophenyl)-2-hydroxyiminoacetonitrile (46.9 g, mp 45°–49° C.) precipitated and was collected by filtration.

A stirred solution of 2-(4-fluorophenyl)-2-hydroxyiminoacetonitrile (42.8 g, 0.26 mole) in 200 ml of pyridine was cooled to 0° C., and p-toluenesulfonyl chloride (76.0 g, 0.39 mole) was added portionwise. Upon complete addition, the reaction mixture was stirred at 0°–5° C. for one hour and then stored in a refrigerator for 16 hours. The resultant slurry was poured into a mixture of ice and water and stirred for 30 minutes. The mixture was then filtered and the white filter cake dried under vacuum without heat to give 2-(4-fluorophenyl)-2-(4-methylphenylsulfonyloxy)iminoacetonitrile (77.3 g, mp 129°–140° C.).

Under a nitrogen atmosphere, a stirred suspension of 2-(4-fluorophenyl)-2-(4-methylphenylsulfonyloxy)iminoacetonitrile (64.0 g, 0.2 mole) and triethylamine (61.8 g, 0.61 mole) in 1 l of absolute ethanol was cooled to 5° C. Ethyl 2-mercaptoacetate (26.8 g, 0.22 mole) was added dropwise over a four hour period. The reaction mixture was then stirred for 16 hours and warmed to room temperature. The reaction mixture was concentrated and poured into 2 l of ice water. The resultant precipitate was collected by filtration. The solid filter cake was washed with water and dried. The solid was dissolved in 1.5 l of boiling heptane, and the solution was slurried with silica gel. The hot mixture was filtered; on cooling the filtrate, the solid recrystallized and was collected by filtration, washed with heptane, and dried to give ethyl 3-(4-fluorophenyl)-4-amino-5-isothiazolecarboxylate (22.0 g, mp 137°–139° C.).

The nmr spectrum was consistent with the proposed structure. Analysis: Calc'd for $C_{12}H_{11}FN_2O_2S$: C 54.20; H 4.16; N 10.52; Found: C 54.43; H 4.45; N 10.39.

Similarly, the following compounds were prepared:

| Example | Name | mp °C. |
| --- | --- | --- |
| 1 | 3-Phenyl-4-amino-5-isothiazolecarboxylic acid | 221–223 |
| 2 | 3-(4-Chlorophenyl)-4-amino-5-isothiazolecarboxylic acid | 233–235 |
| 3 | 3-(4-Fluorophenyl)-4-amino-5-isothiazolecarboxylic acid | 256–258 |
| 4 | 3-(4-Nitrophenyl)-4-amino-5-isothiazolecarboxylic acid | 240–243 |
| 5 | Methyl 3-phenyl-4-amino-5-isothiazolecarboxylate | 108–111 |
| 6 | Methyl 3-(4-chlorophenyl)-4-amino-5-isothiazolecarboxylate | 151–154 |

-continued

| Example | Name | mp °C. |
|---------|------|--------|
| 7 | Methyl 3-(4-bromophenyl)-4-amino-5-isothiazolecarboxylate | 156–158 |
| 8 | Methyl 3-(4-fluorophenyl)-4-amino-5-isothiazolecarboxylate | 120–121 |
| 9 | Methyl 3-(4-methylphenyl)-4-amino-5-isothiazolecarboxylate | 143–145 |
| 10 | Methyl 3-(4-methoxyphenyl)-4-amino-5-isothiazolecarboxylate | 127–128 |
| 11 | Methyl 3-(4-nitrophenyl)-4-amino-5-isothiazolecarboxylate | 185–188 |
| 12 | Ethyl 3-phenyl-4-amino-5-isothiazolecarboxylate | 46–48 |
| 13 | Ethyl 3-(4-chlorophenyl)-4-amino-5-isothiazolecarboxylate | 119–121 |
| 14 | Ethyl 3-(4-bromophenyl)-4-amino-5-isothiazolecarboxylate | 103–104 |
| 15 | Ethyl 3-(2-fluorophenyl)-4-amino-5-isothiazolecarboxylate | Liquid |
| 16 | Ethyl 3-(3-fluorophenyl)-4-amino-5-isothiazolecarboxylate | 148–150 |
| 18 | Ethyl 3-(4-methylphenyl)-4-amino-5-isothiazolecarboxylate | 51–52 |
| 19 | Ethyl 3-(3-trifluoromethylphenyl)-4-amino-5-isothiazolecarboxylate | 82–85 |
| 20 | Ethyl 3-(4-trifluoromethylphenyl)-4-amino-5-isothiazolecarboxylate | 124–126 |
| 21 | Ethyl 3-(2-methoxyphenyl)-4-amino-5-isothiazolecarboxylate | 128–130 |
| 22 | Ethyl 3-(4-methoxyphenyl)-4-amino-5-isothiazolecarboxylate | 87–88 |
| 23 | Ethyl 3-(4-difluoromethoxyphenyl)-4-amino-5-isothiazolecarboxylate | 116–118 |
| 24 | Ethyl 3-(4-thiomethylphenyl)-4-amino-5-isothiazolecarboxylate | Solid |
| 25 | Ethyl 3-(3-nitrophenyl)-4-amino-5-isothiazolecarboxylate | 164–167 |
| 26 | Ethyl 3-(4-aminophenyl)-4-amino-5-isothiazolecarboxylate | 205–208 |
| 27 | Ethyl 3-(4-phenylphenyl)-4-amino-5-isothiazolecarboxylate | 152–154 |
| 28 | Propyl 3-phenyl-4-amino-5-isothiazolecarboxylate | 58–61 |
| 29 | Propyl 3-(4-chlorophenyl)-4-amino-5-isothiazolecarboxylate | 69–71 |
| 30 | Propyl 3-(4-bromophenyl)-4-amino-5-isothiazolecarboxylate | 65–68 |
| 31 | Propyl 3-(4-fluorophenyl)-4-amino-5-isothiazolecarboxylate | 70–73 |
| 32 | Propyl 3-(4-methylphenyl)-4-amino-5-isothiazolecarboxylate | 58–61 |
| 33 | Propyl 3-(4-methoxyphenyl)-4-amino-5-isothiazolecarboxylate | 155–158 |
| 34 | Propyl 3-(4-nitrophenyl)-4-amino-5-isothiazolecarboxylate | 205–208 |
| 35 | 1-Methylethyl 3-(4-chlorophenyl)-4-amino-5-isothiazolecarboxylate | 86–88 |
| 36 | Butyl 3-phenyl-4-amino-5-isothiazolecarboxylate | Liquid |
| 37 | Butyl 3-(4-chlorophenyl)-4-amino-5-isothiazolecarboxylate | 57–60 |
| 38 | Butyl 3-(4-bromophenyl)-4-amino-5-isothiazolecarboxylate | 58–61 |
| 39 | Butyl 3-(4-fluorophenyl)-4-amino-5-isothiazolecarboxylate | 58–60 |
| 40 | Butyl 3-(4-methylphenyl)-4-amino-5-isothiazolecarboxylate | 62–65 |
| 41 | Butyl 3-(4-methoxyphenyl)-4-amino-5-isothiazolecarboxylate | 202–205 |
| 42 | Butyl 3-(4-nitrophenyl)-4-amino-5-isothiazolecarboxylate | 250–253 |
| 43 | Butyl 3-(4-phenylphenyl)-4-amino-5-isothiazolecarboxylate | 118–122 |
| 44 | Hexyl 3-(4-nitrophenyl)-4-amino-5-isothiazolecarboxylate | 92–94 |
| 45 | Heptyl 3-(4-chlorophenyl)-4-amino-5-isothiazolecarboxylate | 45–48 |
| 46 | Heptyl 3-(4-nitrophenyl)-4-amino-5-isothiazolecarboxylate | 108–110 |
| 47 | Phenylmethyl 3-(4-chlorophenyl)-4-amino-5-isothiazolecarboxylate | 102–105 |
| 48 | 3-(4-Chlorophenyl)-5-isothiazolecarboxamide | 205–207 |
| 49 | N—Ethyl-3-phenyl-4-amino-5-isothiazolecarboxamide | 88–90 |
| 50 | N—Ethyl-3-(4-chlorophenyl)-4-amino-5-isothiazolecarboxamide | 161–162 |
| 51 | N—Ethyl-3-(4-bromophenyl)-4-amino-5-isothiazolecarboxamide | 172–175 |
| 52 | N—Ethyl-3-(4-fluorophenyl)-4-amino-5-isothiazolecarboxamide | 139–141 |
| 53 | N—Ethyl-3-(4-methylphenyl)-4-amino-5-isothiazolecarboxamide | 132–135 |
| 54 | N—Ethyl-3-(4-methoxyphenyl)-4-amino-5-isothiazolecarboxamide | 120–123 |
| 55 | N—Ethyl-3-(4-nitrophenyl)-4-amino-5-isothiazolecarboxamide | 158–160 |
| 56 | N—Ethyl-3-(4-phenylphenyl)-4-amino-5-isothiazolecarboxamide | 168–171 |
| 57 | N—(2-Hydroxyethyl)-3-(4-chlorophenyl)-4-amino-5-isothiazolecarboxamide | 184–188 |
| 58 | N—(2-Acetoxyethyl)-3-(4-chlorophenyl)-4-amino-5-isothiazolecarboxamide | 123–126 |

In the normal use of the aforesaid nematicidal 3-aryl-4-amino-5-isothiazole derivatives, the nematicidal compounds usually will not be employed free from admixture or dilution, but ordinarily will be used in a suitable formulated nematicidal composition compatible with the method of application and comprising a nematicidally effective amount of at least one of said nematicidal compounds. Said nematicidal compounds, like most pesticidal agents, may be blended with the agriculturally acceptable surface-active agents and carriers normally employed for facilitating the dispersion of active ingredients, recognizing the accepted fact that the formulation and mode of application of a nematicidal compound may affect the activity of the material. The present nematicidal compounds may be applied, for example, as sprays, dusts, or granules to the area where pest control is desired, the type of application varying of course with the pest and the environment. Thus, the nematicidal compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for said nematicidal compounds. The granule particles are relatively large, a diameter of about 400–2500 microns typically. The particles are either impregnated with the nematicidal compound from solution or coated with the compound, adhesive sometimes being employed. Granules generally contain 0.05–10%, preferably 0.5–5%, active ingredient as the nematicidally effective amount. A typical granular formulation employed for evaluation purposes contains 95% attapulgite clay (24/48 mesh) and 5% ethyl 3-(4-fluorophenyl)-4-amino-5-isothiazolecarboxylate.

Dusts are admixtures of said nematicidal compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the nematicide. These finely divided solids have an average particle size of less than about 50 microns. A typical dust formulation useful for controlling nematodes contains by weight 5 parts ethyl 3-(4-fluorophenyl)-4-amino-5-isothiazolecarboxylate, 91.2 parts attapulgite clay, 1.9 parts sodium lignosulfonate, and 1.9 parts sodium alkylnaphthalene sulfonate.

The nematicidal compounds of the present invention may be made into liquid concentrates by dissolution or emulsification in suitable liquids and into solid concentrates by admixture with talc, clays, and other known solid carriers used in the pesticide art. The concentrates are compositions containing, as a nematicidally effective amount, about 5–50% the nematicidal compound and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts. Typical carriers for solid concentrates (also called wettable powders) include fuller's earth, clays, silicas, and other highly absorbent, readily wetted inorganic diluents.

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the nematicidal compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the nematicidal composition.

Other useful formulations include simple solutions of the active ingredient in a solvent in which it is completely soluble at the desired concentration, such as acetone or other organic solvents.

A nematicidally effective amount of said nematicidal compound in a nematicidal composition diluted for application is normally in the range of about 0.001% to about 8% by weight. Many variations of spraying and dusting compositions known in the art may be used by substituting said nematicidal compounds of this invention into compositions known or apparent to the art.

The nematicidal compositions of this invention may be formulated with other active ingredients, including insecticides, other nematicides, acaricides, fungicides, plant growth regulators, fertilizers, etc. In using the compositions to control nematodes, it is only necessary that a nematicidally effective amount of at least one of said nematicidal compounds be applied to the locus where control is desired, generally a soil locus where agricultural crops are grown. When applied to soil, it is advantageous to mix or incorporate the nematicidal compound into the soil. Liquid nematicidal compositions may be injected into the soil as fumigants or sprayed on the surface. Solid compositions may be applied by broadcasting or in bands. For most applications, a nematicidally effective amount will be about 2 to 12 kg per hectare.

The nematicidal compounds were evaluated for nematicidal activity against the root-knot nematode (*Meloidogyne incognita*), the stunt nematode (*Tylenchorhynchus claytoni*), and the lesion nematode (*Pratylenchus penetrans*) using aqueous acetone solutions or 5 weight percent dust formulations made up as follows and ground to fine powders:

Nematicidal compound (100% active basis): 5 parts
Base: 95 parts
 96%-attapulgite clay
 2%-highly purified sodium lignosulfonate (100%)
 2%-powdered sodium alkylnaphthalenesulfonate (75%)

The formulations were tested for activity against root-knot nematode as follows:

Samples of root-knot nematode inoculum were processed for nematodes by using the Caveness and Jensen centrifugal-sugar flotation extraction technique [Caveness, F. E. and Jensen, H. J., "Modification of the Centrifugal Flotation Technique for the Isolation and Concentration of Nematodes and their Eggs from Soil and Plant Tissue", *Proc. Helm. Soc., Washington,* 22, 87–89 (1955)] and mixed with additional steam-sterilized sandy soil so that there were 600 to 800 root-knot nematode larvae and eggs per pot of soil (three inch diameter each, containing approximately 300 g soil). Depending on the total amount of nematode infested soil needed, mixing was accomplished by use of a cement mixer for 5 minutes or a V-shaped rotary mixer for 60 seconds.

Soil so infested was used for soil-incorporated nematicidal studies within 2 days of preparation. The infested soil was treated with formulations to be tested for nematicidal activity by incorporating the formulation in the soil at 25 ppm or less (weight active compound in mg/soil volume in liters). Young tomato plants were planted in this treated, infested soil in three-inch pots. Check plants were planted in the same manner, except untreated, infested soil was used. The formulation base, without active ingredient, was added to infested soil separately and tomato plants grown therein to detect the effects, if any, of chemicals in the formulation base.

At the end of two weeks the roots of all plants were examined and evaluated for galling in comparison to untreated check plants. The results of the tests were expressed in terms of a "Knot Index", a knot index of 4 signifying no control, 3 signifying 25% less swelling on the treated roots than the untreated roots, 2 signifying 50% less swelling, 1 signifying 75% less swelling, and 0 signifying complete control. Between 1 and 0, a knot index of 0.8, 0.5, and 0.4–0.1 signifies 80%, 90%, and 95–99% control, respectively. The results of tests at various rates of application against the root-knot nematode using a number of nematicidal 3-aryl-4-amino-5-isothiazole derivatives appear in Table 1.

Evaluation of compositions of the invention against stunt nematode was carried out by incorporating formulations in soil at various concentrations and then planting a corn seedling therein. Two days thereafter the soil was inoculated with stunt nematode in mixed stages of growth, from larvae to adults. The soil was evaluated for nematode population approximately five weeks after treatment. Untreated check plants showed no nematode control. Results are recorded in Table 2 as "Percent Control" relative to nematode control in the untreated check pot. The results appear in Table 2.

Compositions were also evaluated against lesion nematode, following a procedure similar to that for stunt nematode, but in which pea seedlings were planted instead of corn seedlings, and nematodes were extracted from the root systems, instead of from the soil. Untreated plants showed no nematode control. Results with formulations of the invention are recorded in Table 3.

TABLE 1

| Evaluation Against Root-Knot Nematode | | |
|---|---|---|
| Compound of Ex. | Rate of Application (ppm) | Knot Index |
| 1 | 25 | 0 |
|   | 10 | 4.0 |
| 3 | 10 | 0.2 |
| 4 | 25 | 2.0 |
|   | 10 | 4.0 |
| 5 | 10 | 0.5 |
|   | 10 | 2.0 |
| 6 | 25 | 1.5 |
|   | 25 | 0 |
| 7 | 25 | 0.7 |
|   | 25 | 4.0 |
|   | 10 | 0.8 |
|   | 10 | 4.0 |
| 8 | 25 | 0.5 |
| 9 | 25 | 1.0 |
| 10 | 25 | 0 |
| 11 | 25 | 1.0 |
| 12 | 25 | 0.8 |
| 13 | 25 | 0.8 |
| 14 | 25 | 0 |
| 15 | 25 | 2.0 |
| 16 | 25 | 2.0 |
| 17 | 25 | 0 |
| 18 | 25 | 0.8 |
|   | 25 | 2.0 |
|   | 25 | 4.0 |
| 19 | 25 | 0.8 |
| 20 | 25 | 0 |
| 21 | 25 | 1.5 |
| 22 | 25 | 0.9 |
|   | 25 | 3.5 |
| 23 | 25 | 0 |
| 24 | 25 | 2.5 |
|   | 10 | 4.0 |
| 25 | 25 | 3.5 |
|   | 10 | 4.0 |
| 26 | 25 | 2.0 |
| 27 | 25 | 2.5 |
|   | 10 | 4.0 |
| 28 | 25 | 0.3 |
| 29 | 25 | 0.5 |
|   | 25 | 1.5 |
|   | 25 | 4.0 |
| 30 | 25 | 3.0 |
| 31 | 25 | 1.0 |
| 32 | 25 | 1.0 |
| 34 | 25 | 0.5 |
| 35 | 25 | 2.0 |
|   | 25 | 0.3 |
| 36 | 25 | 2.0 |
| 37 | 25 | 0.7 |
| 38 | 25 | 1.0 |
|   | 25 | 4.0 |
|   | 10 | 2.5 |
|   | 10 | 4.0 |
| 39 | 25 | 0.8 |

TABLE 1-continued

| Evaluation Against Root-Knot Nematode | | |
|---|---|---|
| Compound of Ex. | Rate of Application (ppm) | Knot Index |
| 40 | 25 | 0.8 |
|   | 25 | 1.5 |
| 41 | 10 | 0.7 |
|   | 10 | 1.9 |
| 42 | 25 | 0.3 |
|   | 10 | 0 |
|   | 10 | 3.7 |
| 43 | 25 | 2.0 |
|   | 10 | 4.0 |
| 44 | 25 | 1.5 |
| 46 | 25 | 2.5 |
| 48 | 25 | 0.9 |
| 49 | 25 | 1.0 |
| 50 | 10 | 0 |
|   | 10 | 2.7 |
| 51 | 25 | 0.5 |
|   | 25 | 3.0 |
| 52 | 10 | 2.3 |
| 53 | 25 | 4.0 |
|   | 10 | 3.0 |
|   | 10 | 4.0 |
| 54 | 25 | 0.5 |
|   | 25 | 4.0 |
|   | 10 | 3.5 |
|   | 10 | 4.0 |
| 55 | 25 | 4.0 |
|   | 25 | 2.0 |
| 56 | 25 | 2.5 |
| 57 | 25 | 3.0 |
| 58 | 25 | 1.5 |
|   | 25 | 2.0 |

TABLE 2

| Evaluation Against Stunt Nematode[a] | |
|---|---|
| Compound Number | Percent Control[b] |
| 1 | 21.7 |
| 5 | 15 |
| 8 | 31 |
| 12 | 45 |
|   | 38.8 |
| 13 | 65 |
|   | 50.4 |
| 14 | 80.2 |
| 17 | 45 |
|   | 67.2 |
|   | 60.7 |
| 20 | 66.1 |
| 34 | 19 |
| 41 | 0 |
| 42 | 35 |
| 50 | 64 |
| 52 | 30 |

[a]Rate of Application: 15 ppm
[b]Percent = Control $$\left[\left(\frac{\text{Average Population}}{\text{Count in the Check}} - \frac{\text{Average Population}}{\text{Count in the Treatment}}\right) \div \frac{\text{Average Population}}{\text{Count in the Check}}\right] \times 100$$

TABLE 3

| Evaluation Against Lesion Nematode[a] | |
|---|---|
| Compound Number | Percent Control[b] |
| 1 | 75.7 |
| 5 | 48 |
| 8 | 41 |
| 12 | 34 |
| 13 | 70 |
| 14 | 71.9 |

TABLE 3-continued

| Evaluation Against Lesion Nematode[a] | |
|---|---|
| Compound Number | Percent Control[b] |
| 17 | 35 |
|  | 90 |
| 20 | 69.6 |
| 34 | 0 |
| 41 | 37 |
| 42 | 22 |
| 50 | 48 |
| 52 | 48 |

[a]Rate of Application: 15 ppm
[b]Percent = Control $$\left[ \frac{\frac{\text{Population count in check*}}{\text{Weight of roots in check plant}} - \frac{\text{Population count in treatment*}}{\text{Weight of roots in treated plants}}}{\frac{\text{Population Count in check}}{\text{Weight of Roots in Check plant}}} \times 100 \right]$$

What is claimed is:

1. A method of controlling nematodes which comprises applying to or incorporating into nematode-infested soil a nematicidally effective amount of a nematicidal composition containing in admixture with an agriculturally acceptable carrier at least one nematicidal compound of the formula

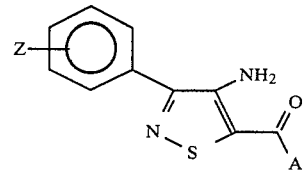

wherein
A is selected from hydroxy, lower alkoxy, phenylmethoxy, and —NHR, where R is hydrogen, straight chain alkyl of 1–4 carbon atoms, 2-hydroxyethyl or 2-acetyloxyethyl; and
Z is selected from hydrogen, halogen, lower alkyl, straight or branched chain alkoxy of 1–4 carbon atoms, difluoromethoxy, thiomethyl, nitro, amino, and phenyl; with the proviso that Z is not 2-bromo or 4-nitro when A is ethoxy.

* * * * *